(12) United States Patent
Nigroni et al.

(10) Patent No.: US 6,679,829 B2
(45) Date of Patent: Jan. 20, 2004

(54) INTRA-AORTIC BALLOON PUMP HAVING IMPROVED AUTOMATED ELECTROCARDIOGRAM BASED INTRA-AORTIC BALLOON DEFLATION TIMING

(76) Inventors: Paul Nigroni, 29 Borman Dr., Wanaque, NJ (US) 07465; Lara Sarraf, 54 Waldwick Ave., Waldwick, NJ (US) 07463

( * ) Notice: Subject to any disclaimer, the term of this patent is extended or adjusted under 35 U.S.C. 154(b) by 101 days.

(21) Appl. No.: 09/850,337

(22) Filed: May 7, 2001

(65) Prior Publication Data

US 2001/0034469 A1 Oct. 25, 2001

Related U.S. Application Data

(63) Continuation-in-part of application No. 09/315,482, filed on May 20, 1999, now Pat. No. 6,290,641.

(51) Int. Cl.$^7$ ................................................ A61M 1/12
(52) U.S. Cl. ........................................................ 600/18
(58) Field of Search .......................................... 600/18

(56) References Cited

U.S. PATENT DOCUMENTS

| | | | |
|---|---|---|---|
| 3,720,199 A | 3/1973 | Rishton et al. | ............... 600/18 |
| 4,362,150 A | 12/1982 | Lombardi, Jr. et al. | ....... 600/18 |
| 4,809,681 A | 3/1989 | Kantrowitz et al. | .......... 600/17 |
| 5,169,379 A | 12/1992 | Freed et al. | .................. 600/18 |
| 6,132,363 A | * 10/2000 | Freed et al. | .................. 600/16 |

OTHER PUBLICATIONS

Excerpts from The Bard® TransAct™ System For Aortic Counterpulsation Theray H–8000 Intra–Aortic Balloon Pump Operating Manual including (1)the Table of Contents, (2) p. 2–24 of Section entitled "Atrial Fibrilation and Other Erratic Rhthyms", and (3) p. 7–11 of Section entitled "Troubleshooting Alarm Messages".

* cited by examiner

Primary Examiner—Carl Layno
(74) Attorney, Agent, or Firm—J. Gary Mohr

(57) ABSTRACT

An intra-aortic balloon pump (IABP) having improved automated electrocardiogram (ECG) based intra-aortic balloon deflation timing. Said IABP capable of automatically determining to either deflate the intra-aortic balloon upon the detection of the next cardiac cycle (non-predictive deflation) or at an earlier point derived from predicting the occurrence of the next cycle (predictive deflation). This automated determination is based upon a quantitative assessment of the performance of the intra-aortic balloon pump in predicting the prevailing cardiac rhythm.

8 Claims, 3 Drawing Sheets ly with respect to the cardiac cycle.
INTRA-AORTIC BALLOON PUMP HAVING IMPROVED AUTOMATED ELECTROCARDIOGRAM BASED INTRA-AORTIC BALLOON DEFLATION TIMING

RELATED APPLICATIONS

This is a continuation in part application of U.S. patent application Ser. No. 09/315,482 filed May 20, 1999 now U.S. Pat. No. 6,290,641.

BACKGROUND OF THE INVENTION

1. Field of the Invention

The invention relates to an intra-aortic balloon pump having improved automated electrocardiogram (ECG) based intra-aortic balloon deflation timing. More particularly, the invention relates to an intra-aortic balloon pump capable of basing the decision of automatically activating and deactivating non-predictive deflation upon a quantitative assessment of the predictive performance of the intra-aortic balloon pump for the prevailing cardiac rhythm.

2. Description of the Prior Art

It is well-known in the art, as described in, for example, the specification of U.S. Pat. No. 4,362,150, to provide cardiac assistance by introducing a balloon into the thoracic aorta of a patient and causing the balloon to inflate and deflate in anti-phase with the contraction of the patient's heart. A balloon of this type is inflated at the beginning of diastole, in order to increase the blood flow to the coronary and carotid arteries. The balloon is then deflated just prior to the start of systole, in order to reduce the load on the left ventricle. It is essential that cardiac activity be sensed reliably to ensure that the balloon is inflated and deflated accurately with respect to the cardiac cycle.

Methods of sensing cardiac activity include analysis of aortic pressure and/or analysis of the electrocardiogram. It is known in the art, as described in U.S. Pat. No. 5,169,379, to combine means for effecting such analysis with the aforementioned intra-aortic balloon (IAB) apparatus.

The focus of the present invention is the automatic control of deflation timing of the intra-aortic balloon. Using the ECG as a time-base, a maximum reduction in end diastolic pressure is achieved when IAB deflation begins in advance of the start of the next cardiac cycle, i.e. R-wave. This deflation modality will hereinafter be referred to as "predictive" deflation since the start of the next cardiac cycle must be predicted, based on prior beat intervals. The goal of predictive deflation is to predict the start of the next cardiac cycle and to completely deflate the balloon in advance of the next predicted beat. Algorithms for predicting the start of the next cardiac cycle for a regular cardiac rhythm are generally known in the art of balloon pumping.

One difficulty with using a standard predictive deflation algorithm for control of the intra-aortic balloon is the potential onset of cardiac rhythm variations. In the presence of random and chronically irregular rhythms, such as atrial fibrillation, accurate prediction of the next ECG beat is not possible. Prediction can be made with only limited statistical probability. Accordingly, such random dysrhythmic patterns are generally managed by having the intra-aortic balloon pump deflate the intra-aortic balloon on the leading edge of the R-wave. This method of intra-aortic balloon deflation will hereinafter be referred to as R-wave deflation. R-wave deflation is a non-predictive deflation method which produces a later deflation of the intra-aortic balloon than that produced by predictive deflation. The advantage of setting the intra-aortic balloon pump to R-wave deflation mode in the presence of an irregular rhythm, however, is that deflation of the intra-aortic balloon begins precisely upon the identification of the next R-wave, regardless of the variance of the rhythm. This enables the intra-aortic balloon pump to consistently augment the entire diastolic interval and unload the next impending left ventricular contraction.

It is not necessary that all rhythm variations be managed by switching to R-wave deflation. For example, algorithms are known in the art for identifying transient disturbances (dysrhythmia) such as premature ventricular complexes (PVCs), including isolated PVCs and Couplets, and also for recognizing sudden changes in heart rates. These rhythm variations can be rapidly identified and are typically followed by a predictable beat pattern. Accurate prediction of such beats, after a brief initial learning phase period, is often possible.

As indicated above, intra-aortic balloon pumps presently on the market are automated. The intra-aortic balloon is controlled by a predictive algorithm in situations involving regular rhythms and at least one pump will automatically adopt R-wave deflation upon degradation of the rhythm beyond a threshold level. Bard'S TRANSACT IABP, for example, incorporates an algorithm for determining when to switch to and from R-wave deflation, which is based upon beat-to-beat, i.e. R—R interval, variability.

More specifically, if the Bard intra-aortic balloon pump detects a large beat-to-beat variation in cardiac interval for 8 out of the last 16 beats intervals then the Bard pump abandons the use of predictive deflation and adopts R-wave deflation control. A major drawback to this method is that the decision to abandon the predictive mode is independent of the success that the intra-aortic balloon pump is having in following the timing variations associated with the rhythm disturbance. For example, if a patient's rhythm was such that a premature ventricular contraction occurred on every other beat, and the Bard intra-aortic balloon pump is designed to successfully track this rhythm, the Bard pump would still abandon the predictive mode because the above described requirements have been met, i.e at least 8 out the past 16 R—R intervals were sufficiently variable to trigger the switch from the predictive deflation mode to the R-wave deflation mode.

SUMMARY OF THE INVENTION

Accordingly, it is an object of the present invention to produce an intra-aortic balloon pump which monitors the performance of its predictive mode and automatically switches to a non-predictive deflation mode, such as R-wave deflation, when predictive deflation tracking is compromised by a dysrhythmia, and remains in this deflation modality as long as the cardiac rhythm cannot be accurately predicted.

Note that hereinafter any references made to R-wave deflation are also applicable to other non-predictive deflation modalities. An example of a non-predictive deflation mode other than R-wave, is P-wave deflation. In this deflation modality, the IAB is deflated on or after the detected P-wave of the ECG.

The invention is a highly automated intra-aortic balloon pump capable of basing its decision of automatically activating and deactivating R-wave deflation timing, or another non-predictive deflation, on the predictive performance of the intra-aortic balloon pump. Assessing the predictive performance of the IABP can be achieved by comparing the accuracy of each R-wave prediction to the actual occurrence of the R-wave. Scoring is one means to account for accuracy.

In a scoring arrangement, early and late predictions are scored more heavily (penalized) than accurate predictions. Early or late R-wave predictions that occur at the initial onset of a recognizable dysrhythmic heartbeat pattern or rate change, however, are not included in the score. Once a critical score is reached the R-wave deflation mode is automatically activated. Scoring continues in R-wave deflation to signal when to switch back to predictive deflation. Note that the present invention is not limited to a scoring methodology, but encompasses any methodology to gauge or index performance. Another means of activating R-wave deflation would be to weigh the effect of early deflates on the total available time for diastolic augmentation. Early predictions result in early deflates, and can significantly reduce the utilization of the time available for augmenting diastole and compromise unloading of the left ventricle.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

DETAILED DESCRIPTION OF THE PREFERRED EMBODIMENTS

Figure 1:
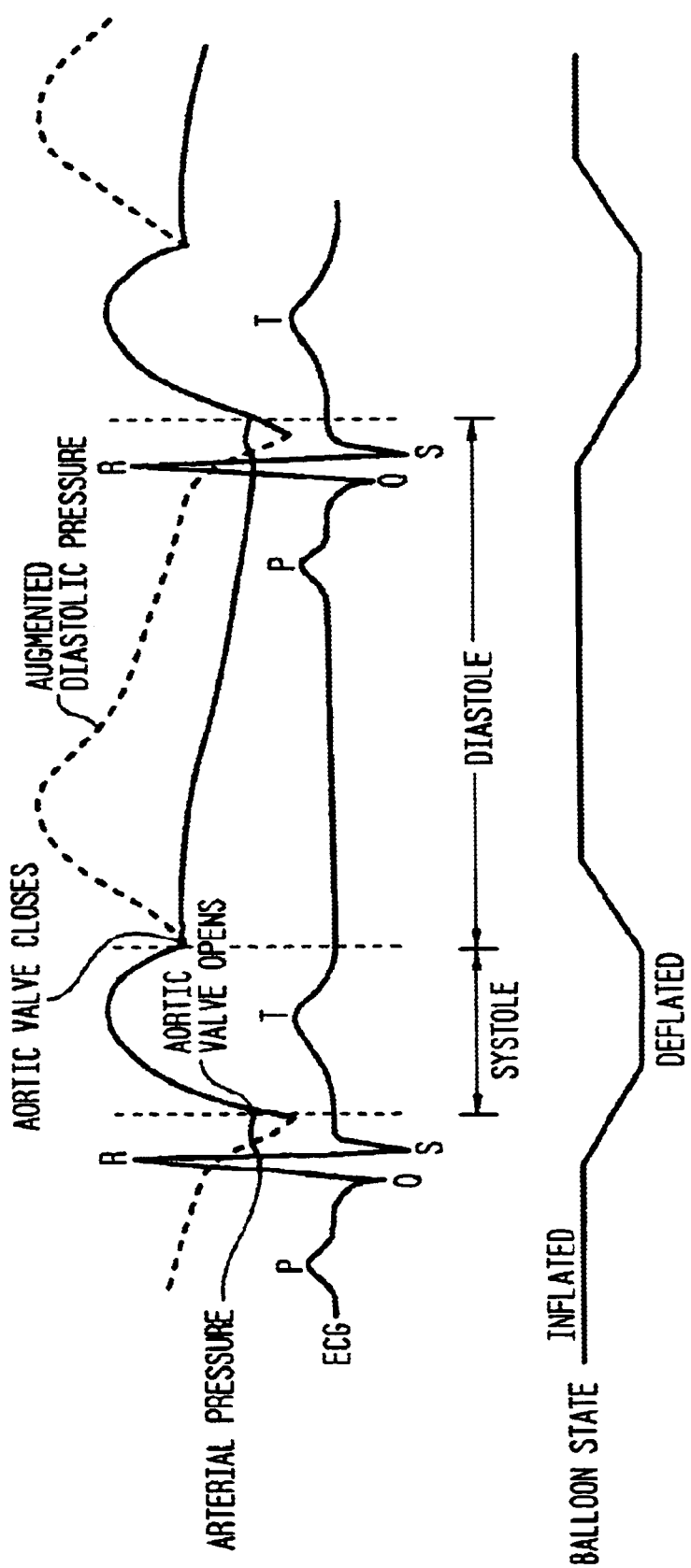
FIG. 1 is a plot of ECG, blood pressure, and balloon state versus time.

Before describing the present invention in detail, reference will be made to FIG. 1, which is useful in understanding the principle of the invention.

Methods of monitoring cardiac activity for timing of the inflation and deflation of an intra-aortic balloon include measurement of aortic pressure and measurement based on an electrocardiographic (ECG) signal. FIG. 1 illustrates a plot of ECG, blood pressure, and balloon state versus time in R-wave deflation. Both augmented (dotted lined) and unaugmented (solid line) diastolic arterial pressure waveforms are shown. The ECG R-wave gives advance notice of the opening of the aortic valve, and the dicrotic notch appears in the aortic pressure at the closure of the aortic valve. Accordingly, the intra-aortic balloon, following its insertion into the aorta, is adjusted to inflate at the occurrence of the dicrotic notch and deflate relative to the next impending R-wave. Conventionally, due to the finite amount of time required for deflation, it is necessary to accurately predict when the R-wave will occur and to begin balloon deflation prior to the identification of the next R-wave (i.e. earlier than shown in FIG. 1).

Intra-aortic balloon pumps presently on the market are "automated" to the extent that they are capable of predicting when the next R-wave will occur for rhythmic beats and for some rhythms displaying transient disturbances, such as premature ventricular complexes (PVCs). In the presence of rhythmic beats the "automated" balloon pump is typically programmed and adjusted to initiate deflation of the balloon prior to the next R-wave so as to allow for complete or near complete balloon deflation prior to the start of systole. In the presence of random and chronically irregular rhythms, such as atrial fibrillation, however, prediction of the next R-wave is not possible. In such situations the balloon pumps are generally operated to deflate the balloon on the detected leading edge of the R-wave (R-wave deflation), as illustrated in FIG. 1. R-wave deflation results in the heart ejecting blood into a blood vessel containing an only partially deflated balloon. The advantage to R-wave deflation, however, is that deflation begins upon the identification of the next R-wave, regardless of the variance of the rhythm, permitting the pump to consistently augment the entire diastolic interval and unload the impending left ventricular contraction.

Reverting to R-wave deflation in the presence of random and chronically irregular rhythms is often preferred. Reverting to R-wave deflation in the presence of regular or only transient rhythm disturbances, specifically those recognizable by the balloon pump, however, is unnecessary. The present invention comprises a balloon pump which bases its decision of alternating between a predictive deflation mode and R-wave deflation mode, or an alternate non-predictive mode, as indicated earlier, on the predictive performance of the balloon pump. The basic principle is for the pump to assess and quantify its own performance in predicting the prevailing cardiac rhythm. This is in contrast to Bard'S TRANSACT IABP which bases it decision of alternating between predictive deflation mode and R-wave deflation mode simply on the R—R interval variability.

Figure 2:
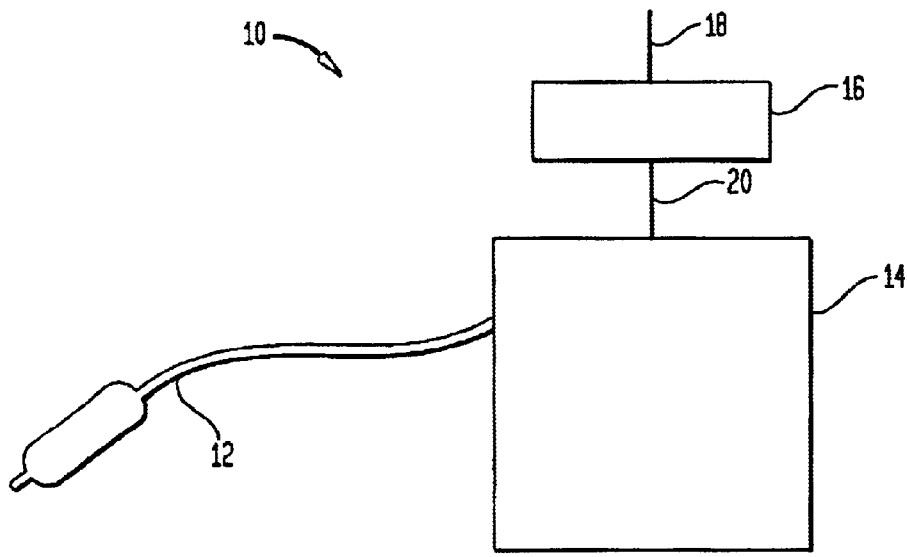
FIG. 2 is plan view of the intra-aortic balloon connected to an intra-aortic balloon pump having a control logic module.

FIG. 2 illustrates an intra-aortic balloon pump (IABP) system 10 having improved automated ECG based IAB deflation timing, comprising an intra-aortic balloon (IAB) catheter 12, an inflation/deflation means 14, and a control logic module 16. The IAB catheter 12, for insertion into the aorta of a patient (not shown), is connected to the inflation/deflation means 14. The inflation/deflation means 14, preferably a pneumatic drive module, is in communication with the control logic module 16 via an inflate/deflate line 20. The control logic module 16 has an ECG input line 18 and may also have an inflation and deflation adjustment control line (not shown). The control logic module 16 uses information communicated via the ECG input line 18, in conjunction with the inflation and deflation adjustment control (not shown), to determine when to output an inflate signal or a deflate signal to the inflation/deflation means 14 via the inflate/deflate line 20. Upon command from the control logic module 16, inflation/deflation means 14 inflates or deflates the IAB catheter 12.

The control logic module 16 is programmed to operate the inflation/deflation means 14 in predictive deflation mode as long as it is successfully tracking the patient's heart beat. Algorithms for predictive deflation in regular rhythms and also in certain transient rhythms are known in the art of intra-aortic balloon pumping. The control logic module 16 scores the accuracy of the deflation based upon a R—R interval prediction relating to the actual R—R interval (block 30 in FIG. 3). Note that the scope for beat-to-beat interval determination is not limited to the R—R interval but includes the use of any other repeatable events in the cardiac cycle. Also note that the scope of determining predictive timing performance is not limited exclusively to a scoring methodology but includes any means of determining, deriving, or computing an index of performance.

Figure 1A:
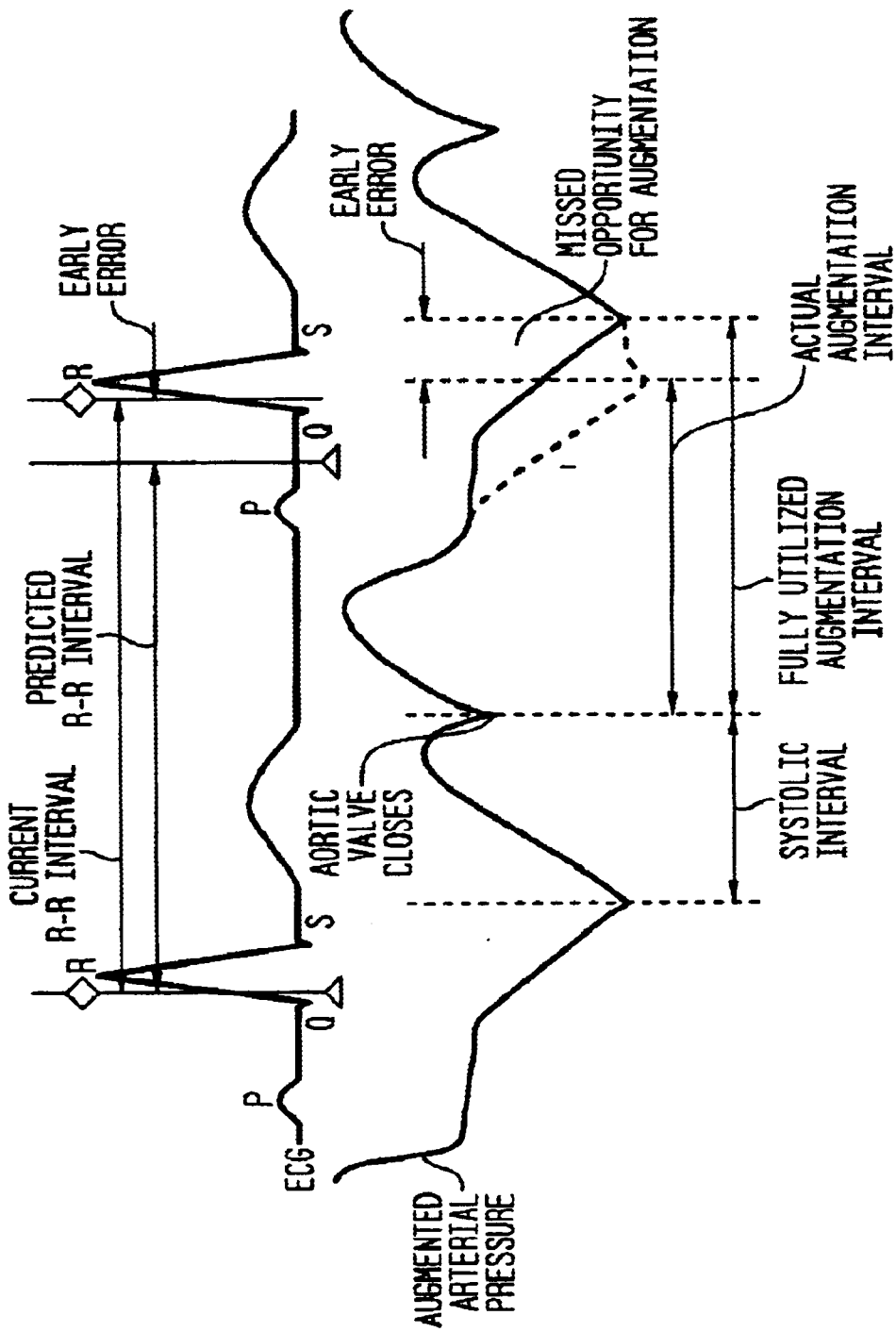
FIG 1A is a plot of ECG and augmented blood pressure versus time illustrating the effect of an early deflate.

FIG. 1A comprises an ECG waveform and an Augmented Arterial Pressure waveform illustrating an early beat prediction by control logic module 16. Upon the detection of each R-Wave, control logic module 16 predicts when the next R-Wave should occur given the current beat pattern (see the ECG Predicted R—R Interval in FIG. 1A). This prediction permits IAB deflation to be scheduled in advance of the occurrence of the next beat. The example in FIG. 1A illustrates that the actual cardiac interval was longer than predicted, resulting in an early balloon deflation and a Missed Opportunity for Augmentation (see the ECG Current R—R Interval and the Augmented Arterial Pressure Actual Augmentation Interval). The resulting deflation timing error is equivalent in magnitude to the prediction error.

Control logic module 16 determines the impact that prediction errors are having upon fully utilizing diastole as an opportunity to augment coronary pressure. One methodology is to compare the magnitude of the prediction errors, and consequently deflation timing errors, to the total diastolic augmentation time available. The ratio of these measures provides an index of utilization. An alternative method is to compare actual to fully utilized augmentation area under the respective diastolic portions of the blood pressure waveforms. Note that this requires the addition of an Arterial Blood Pressure input to logic module 16 in FIG. 2, which is not shown. Accurate predictions facilitate augmentation of the entire diastolic interval. However, early deflation will occur should the prediction of the next cardiac cycle be early. In response to significantly large and persistent errors, control logic module 16 will switch to R-wave deflation mode. Conversely, if a predictive activation threshold is reached, while in R-Wave deflation mode, the pump control module will switch deflation control back to the predictive mode. The choice to readopt predictive deflation control may be based on any of the above techniques for assessing the impact that prediction errors are having upon fully utilizing diastole as an opportunity to augment coronary pressure. Furthermore, the choice to readopt predictive deflation control does not necessarily have to occur at the same threshold level for which it was originally discarded.

Figure 3:
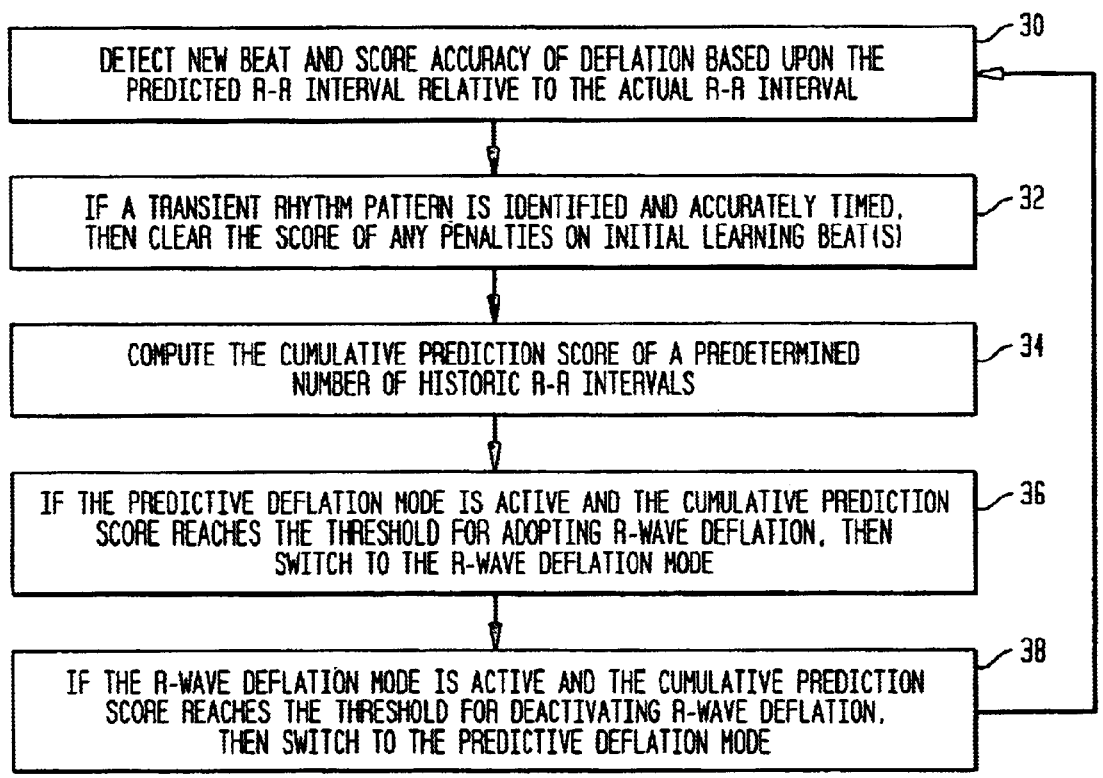
FIG. 3 is a flow chart illustrating the method of activating and deactivating R-wave deflation based on a scoring arrangement.

FIG. 3 is a flow chart, each block illustrating one step in the method of activating and deactivating the R-wave deflation mode based on a scoring arrangement. In the following example of a scoring methodology, a tolerance window following the predicted R-wave event is such that moderately early predictions are not penalized:

A score of 0 for an accurate prediction;

A score of 1 or 2 for a very early prediction resulting in a very early deflation;

A score of 0 for a moderately late prediction, not resulting in an R-wave deflation; and A score of 1 for a "very late" prediction resulting in an R-wave deflation.

The term "very early" is applicable in this example when the prediction results in a deflation so early, it significantly reduces the time available for diastolic augmentation. Significant occurrences of such very early deflates minimize blood flow to the coronary and carotid arteries and compromise unloading on the left ventricle. Notice should be taken that the above scoring arrangement is merely an example and that the "early" and "late" weighting may be varied based upon the clinical significance of the timing variations. The present invention encompasses other such arrangements. Notice should further be taken that an operator has the ability to disable automatic activation of the R-wave deflation mode and assume manual control of the deflation timing mode.

The control logic module 16 keeps track of the cumulative prediction scoring of a predetermined number of historic R—R intervals (block 34 in FIG. 3). If the cumulative prediction score reaches a predetermined threshold for adopting R-wave deflation, the control logic module 16 activates the R-wave deflation mode (block 36 in FIG. 3). Scoring continues in this mode until the cumulative prediction score reaches the predetermined threshold for deactivating R-wave deflation, upon which the control logic module 16 reinitiates predictive deflation (block 38 in FIG. 3). The threshold limits for activating and deactivating R-wave deflation mode may be predetermined values based upon the desired clinical sensitivity.

When the non-predictive activation threshold is reached the control logic module 16 will switch to a non-predictive mode, such as R-wave deflation mode. In this example, the control logic module 16 will switch to R-wave deflation mode if the cumulative prediction score of the past 16 R—R intervals is greater than or equal to 8, otherwise, it remains in the predictive deflation mode. Further in this example hysteresis is employed, once in the R-wave deflation mode the control logic module 16 will switch back to predictive deflation mode when the predictive activation threshold is reached. In this example, predictive activation threshold is reached when the score of the last 16 R—R intervals becomes less than 5.

Control logic module 16 is capable of identifying and predicting certain transient rhythm patterns. In the process of identifying a transient rhythm disturbance, one or more initial R—R intervals may not be predictable. This is unavoidable because these R—R intervals occur at the onset of the new pattern, i.e. they are part of the identification or learning phase. Therefore, when the rhythm disturbance is such that it exhibits a pattern identified by control logic module 16, the scoring of the pattern is reevaluated (block 32 in FIG. 3). This reevaluation is performed to ensure that the control logic module 16 does not switch to R-wave deflation mode when it is accurately managing a predictable rhythm disturbance. In the example presented, R-wave predictions scored heavily (1 or 2) during the onset of the pattern are not penalized (reset to 0) if the pattern is successfully identified. Note that the reevaluation technique may be used in conjunction with other methods of determining when to switch to and from R-wave deflation mode.

Examples of possible recognizable rhythm disturbances include a premature ventricular contraction (PVC) pattern, characterized by one significantly short R—R interval followed by a longer than normal R—R interval, or a Couplet (PVC pair) pattern, characterized by two successive significantly short R—R intervals followed by a longer than normal R—R interval, and the onset of a faster or slower heartbeat rate. The term "recognizable" in reference to a PVC, for example, means that upon detection of a premature ventricular contraction the control logic module 16 can accurately predict the occurrence of the next R-wave.

As many apparently widely different embodiments of the present invention can be made without departing from the spirit and scope thereof, it is to be understood that the invention is not limited to the specific embodiments thereof except as defined in the appended claims.

What is claimed is:

1. An intra-aortic balloon pump comprising a balloon inflation and deflation means and a control logic module for controlling said balloon inflation and deflation means, said control logic module having a setting in which it bases its decision of automatically activating and/or deactivating a non-predictive deflation mode on its assessment of its performance in a predictive deflation mode, said control logic module assessing the performance of the intra-aortic balloon pump by comparing prediction errors and consequently deflation timing errors to total diastolic augmentation time available.

2. An intra-aortic balloon pump comprising a balloon inflation and deflation means and a control logic module for controlling said balloon inflation and deflation means, said control logic module having a setting in which it bases its decision of automatically activating and/or deactivating a non-predictive deflation mode on its assessment of its performance in a predictive deflation mode, said control logic module assessing the performance of the intra-aortic balloon pump by comparing actual diastolic augmentation for a given beat to the total potential diastolic augmentation that can be realized.

3. The intra-aortic balloon pump as claimed in claim 1 or 2 wherein the non-predictive deflation mode is a P-wave deflation mode.

4. A method for an intra-aortic balloon pump for determining when to automatically switch from a predictive deflation mode to a non-predictive deflation mode, said intra-aortic balloon pump comprising a balloon inflation and deflation means and a control logic module for controlling said balloon inflation and deflation means, said control logic module having a setting in which it bases its decision of automatically activating a non-predictive deflation mode on its assessment of its performance in a predictive deflation mode, said method comprising the steps of:
 a) assessing the performance of the intra-aortic balloon pump in the predictive deflation mode by comparing prediction errors and consequently deflation timing errors to total diastolic augmentation time available; and
 b) switching to the non-predictive deflation mode when a predetermined non-predictive activation threshold is reached, said non-predictive activation threshold being based on the assessment of intra-aortic balloon pump performance in part (a).

5. A method for an intra-aortic balloon pump for determining when to automatically switch from a predictive deflation mode to a non-predictive deflation mode, said intra-aortic balloon pump comprising a balloon inflation and deflation means and a control logic module for controlling said balloon inflation and deflation means, said control logic module having a setting in which it bases its decision of automatically activating a non-predictive deflation mode on its assessment of its performance in a predictive deflation mode, said method comprising the steps of:
 a) assessing the performance of the intra-aortic balloon pump in the predictive deflation mode by comparing actual diastolic augmentation for a given beat to the total potential diastolic augmentation that can be realized; and
 b) switching to the non-predictive deflation mode when a predetermined non-predictive activation threshold is reached, said non-predictive activation threshold being based on the assessment of intra-aortic balloon pump performance in part (a).

6. The method as claimed in claim 4 or 5 wherein the non-predictive deflation mode is a P-wave deflation mode.

7. The method claimed in claim 4 or 5 further comprising the steps of: assessing the performance of the intra-aortic balloon pump in predicting when the next cardiac cycle is to occur while in the non-predictive deflation mode; and switching back to the predictive mode when a predetermined activation threshold being based on a comparison of prediction errors and consequently deflation timing errors to total diastolic augmentation time available.

8. The method as claimed in claim 4 or 5 further comprising the steps of: assessing the performance of the intra-aortic balloon pump in predicting when the next cardiac cycle is to occur while in the non-predictive deflation mode; and switching back to the predictive mode when a predetermined predictive activation threshold is reached, said predictive activation threshold being based on a comparison of actual diastolic augmentation for a given beat to the total potential diastolic augmentation that can be realized.

* * * * *